US006773932B2

(12) United States Patent
Robinson et al.

(10) Patent No.: US 6,773,932 B2
(45) Date of Patent: Aug. 10, 2004

(54) SYSTEM AND METHOD FOR COLLECTING, STORING, AND DISPLAYING PROCESS DATA INCLUDING PARTICLE MEASUREMENT DATA

(75) Inventors: Michael M. Robinson, Vancouver, WA (US); Leif Carlson, Vancouver, WA (US)

(73) Assignee: Seh America, Inc., Vancouver, WA (US)

( * ) Notice: Subject to any disclaimer, the term of this patent is extended or adjusted under 35 U.S.C. 154(b) by 47 days.

(21) Appl. No.: 09/998,257

(22) Filed: Nov. 30, 2001

(65) Prior Publication Data

US 2003/0105546 A1 Jun. 5, 2003

(51) Int. Cl.[7] ............................................... H01L 21/66
(52) U.S. Cl. ......................... 438/14; 438/16; 702/179; 702/182; 702/183; 702/188
(58) Field of Search .................... 438/14, 16; 702/179, 702/180, 182, 183, 184, 185, 186, 188

(56) References Cited

U.S. PATENT DOCUMENTS

| | | | |
|---|---|---|---|
| 5,598,341 A | | 1/1997 | Ling et al. |
| 5,625,816 A | | 4/1997 | Burdick et al. |
| 5,672,230 A | | 9/1997 | Park et al. |
| 5,761,064 A | | 6/1998 | La et al. |
| 6,177,983 B1 | | 1/2001 | Trainer |
| 6,223,098 B1 | | 4/2001 | Cheong et al. |
| 6,233,719 B1 | | 5/2001 | Hardikar et al. |
| 6,259,101 B1 | | 7/2001 | Wexler et al. |
| 6,275,290 B1 | | 8/2001 | Cerni et al. |
| 6,314,379 B1 | | 11/2001 | Hu et al. |
| 6,314,385 B1 | * | 11/2001 | Kim et al. .................. 702/184 |
| 6,319,737 B1 | | 11/2001 | Putnam et al. |
| 6,346,983 B1 | | 2/2002 | Yufa |
| 6,606,582 B1 | * | 8/2003 | Brinkman et al. ............ 438/14 |

OTHER PUBLICATIONS

U.S. patent application Ser. No. 09/536,506, Brinkman et al., filed Mar. 27, 2000.
Website of Particle Measuring Systems, Inc. at http://www.pmeasuring.com; 20 pages dated Feb. 23, 2000 (Copyright 1998–2000) including Aerosol Manifold, LASAIR®Particle Counter, High Sensitivity Liquid In–Situ System, High Pressure Gas Probe, Aerosol Data Acquisition System and Facility Monitoring System.
Matthew J. Brinkman and Allen R. Boyce; Ultrapure Water, Chemicals and Cleanroom Air Particle Measuring Systems Integrating data into standard Facilities Management and Control systems for viewing, trending and control; 7 unnumbered pages including 4 figures; presented at Semiconductor Pure Water and Chemical Conference; Mar. 13–16, 2000, Santa Clara, CA; presented by Boyce/Brinkman.

\* cited by examiner

Primary Examiner—Kevin M. Picardat
(74) Attorney, Agent, or Firm—Alston & Bird LLP (57) ABSTRACT

A system and method are provided for collecting, storing, and displaying a plurality of different types of process data, including accumulated and differential particle counts, from remote locations without requiring manual intervention. The system includes a plurality of particle measuring instruments disposed at respective locations distributed about a facility in order to collect particle data. The system also includes a process data collection device for providing process data other than particle data, such as temperature, pressure or humidity level. The system is interconnected with the plurality of particle measuring instruments and the process data collection device by means of a computer network. As such, the particle data and process data can be provided to a computer network for collection and storage. Thereafter, the particle data and the process data can be remotely displayed at a graphic user interface.

12 Claims, 4 Drawing Sheets

SYSTEM AND METHOD FOR COLLECTING, STORING, AND DISPLAYING PROCESS DATA INCLUDING PARTICLE MEASUREMENT DATA

FIELD OF THE INVENTION

The present invention relates generally to facility management and control systems and, more particularly, to facility management and control systems and methods for use in the semiconductor wafer manufacturing industry to collect process data including particle measurement data from remote locations.

BACKGROUND OF THE INVENTION

In order to monitor and control modern industrial processes, facility management and control systems have been developed. Facility management and control systems collect various types of process data. A facility management and control system can then analyze the process data for quality control purposes as described below.

The measurement instruments that provide the process data are typically distributed throughout the facility with the particular arrangement dependent upon the nature of the process being monitored and the configuration of the facility. In addition, various types of measurement instruments can be employed depending upon the process data that is to be collected. For example, measurement instruments are typically employed to measure process data such as temperatures, pressures, humidity levels, switch positions and the like. While these measurement instruments can operate independently, the process data provided by the measurement instruments that monitor a particular stage of a process are oftentimes collected by a programmable logic controller.

Although the measurement instruments are typically distributed at various locations throughout the facility depending upon the particular stage of the process that is to be monitored, facility management and control systems generally include a computer for collecting and processing the data provided by the various measurement instruments. The computer is typically located at a relatively centralized position, such as within a control room or the like. As such, the computer is generally remote from most, if not all, of the measurement instruments by being positioned in a different room of the same building or in another building altogether. By collecting the data provided by the measurement instruments or, more commonly, by one or more programmable logic controllers with a computer, the data can be more thoroughly analyzed such as by cross-checking or correlating the data obtained by measurement instruments that are designed to monitor different stages of the process.

The computer can process the data in various manners for quality control and other purposes. In this regard, the data can be examined from a historical perspective in an attempt to determine, after the fact, the processing conditions that existed during the fabrication of products that were eventually determined to be of either unusually high quality or unacceptably low quality. In order to avoid fabricating a number of unacceptable products prior to detecting the problem and taking corrective action to bring the process back into tolerance, the computer can compare the current process data to predetermined acceptable ranges of process data. As such, if the process data collected by the measurement instruments falls outside the predetermined range of acceptable process data, the central computer can trigger an alarm such that the process parameters can be quickly adjusted prior to fabricating a large number of unacceptable products.

One example of a process for which a facility management and control system has been developed is the wafer fabrication process. In this process, wafers, such as silicon wafers, undergo a number of different process steps in order to fabricate wafers having the desired characteristics, such as the desired resistivity, surface roughness, etc. A facilities management and control system that includes a computer and a number of distributed measurement instruments is particularly useful for a wafer fabrication process since slight variations in the process parameters can substantially alter the characteristics of the resulting wafers, thereby causing wafers that will be unacceptable to be fabricated as a result of only minor changes in the process parameters. A facilities management and control system is also advantageous for a wafer fabrication process since the throughput of a wafer fabrication process is relatively high such that it is desirable to detect variations in the process parameters as soon as possible in order to reduce the number of unacceptable wafers that are fabricated.

In a wafer fabrication process, one of the most important process parameters is the particle count at different stages. In this regard, wafers are subjected to various environments during the fabrication process, some of which are designed to be ultra-pure environments having relatively few particles or contaminants. For example, at different stages of the fabrication process, a wafer is typically washed with ultra-pure water, exposed to ultra-pure chemicals, subjected to high pressure gas, such as hydrogen or nitrogen, having relatively few particles or subjected to an aerosol having relatively few particles, such as within a cleanroom. During any of these stages of the fabrication process, it is desirable to measure the particles in the particular medium, such as the water, chemical, gas or aerosol.

Two types of particle measurements are accumulated particle counts and differential particle counts. Accumulated particle counts are a running total of the particles, typically having at least a predefined minimum size or diameter, detected within a window of time. Thus, an accumulated particle count is typically the sum of several measurements taken during the window of time. Conversely, differential particle counts measure the change in particles, also typically having at least a predefined minimum size, from one measurement to the next.

These particle measurements can then be used to monitor particle levels and to track changes in the particle levels. Historical trends can be identified and used to analyze particle data correlation with wafer quality and other manufacturing processes. Based upon historical trends and related process data, acceptable operating levels and/or thresholds for accumulated particle counts and differential particle counts can be established to maintain wafer fabrication quality standards. Since the accumulated and differential particle counts each provide somewhat different and useful data, it is therefore desirable to measure and track the accumulated particle counts and differential change in particle counts from measurement to measurement. As such, various particle measurement instruments have been developed and are commercially available to provide these particle counts.

Unfortunately, these conventional particle measurement instruments are generally unable to transmit the data, such as the particle counts, that has been collected to a computer that is remote from the particle measurement instruments in the same manner as other measurement instruments or programmable logic controllers. As such, dedicated computers were oftentimes co-located with the particle measurement instruments in order to collect and characterize the data. In order to correlate the data collected by the particle measurement instruments with the data collected by various other measurement instruments distributed throughout the wafer fabrication facility, technicians would have to manually collect the particle data from the dedicated computers associated with the respective particle measurement instruments distributed throughout the facility, such as by obtaining a printout of the particle data from each dedicated computer or downloading the particle data onto a computer diskette or the like. Typically, the particle data is then manually re-entered into a spreadsheet. By copying other process data from the facilities management and control system, i.e., the process data collected by other measurement instruments, and by exporting this other process data in spreadsheet format, this other process data can be merged with the particle data and the combined data set can be evaluated. As such, the various different types of data collected for the respective stages of the fabrication process can be correlated for training, quality control or other purposes.

As will be apparent, the manual collection and re-entry of the particle data can quickly become time consuming and is subject to errors during the manual re-entry process. As such, attempts have been made to connect the particle measurement instruments to a central computer by utilizing line drivers to transmit the particle data that is provided serially by the particle measurement instruments distributed about the facility to the central computer. Unfortunately, the line drivers are notoriously prone to the introduction of errors, particularly at the relatively high bit rates that would be utilized during the transmission of the particle data.

A facility monitoring system has been developed by Particle Measuring Systems, Inc. (PMS) of Boulder, Colo. that permits the particle data collected by PMS particle measurement instruments to be transmitted to a central computer via a computer network by using TCP/IP protocol. In addition to transmitting the particle data, the PMS particle measurement instruments generally include ports to which other measurement instruments can be connected. The PMS particle measurement instruments can therefore transmit the process data collected by these other measurement instruments along with the particle data to the central computer. For example, measurement instruments that can be connected to a PMS particle measurement instrument include a temperature sensor, a pressure gauge and the like.

Unfortunately, the PMS facility monitoring system does not interface with the measurement instruments of other vendors and therefore does not permit the process data collected by the measurement instruments of other vendors to be transmitted via the computer network for collection by the computer. In addition, the central computer of a PMS facility monitoring system does not interface with measurement instruments designed to measure process data other than particle data unless these other measurement instruments are first connected to a PMS particle measurement instrument, and the process data collected by these other measuring instruments is transmitted along with the particle data by the PMS particle measurement instrument. Thus, the PMS facility monitoring system does not permit measurement instruments that are independent of the PMS particle measurement instruments to separately transmit process data, such as temperatures, pressures, humidity levels, switch positions or the like, via the computer network for processing and correlation with the particle data provided by the PMS particle measurement instruments. As such, it would be desirable to provide a facilities management and control system and method that include a computer network that could communicate in a reliable manner with a variety of measurement instruments, including particle measurement instruments, without requiring manual intervention in order to collect and re-enter the particle data and without requiring all process data to be routed through the particle measurement instruments.

SUMMARY OF THE INVENTION

A system and method are provided for collecting, storing, and displaying particle measurement data from a plurality particle measuring instruments and other process data from process data collection devices. With respect to the particle measurement data, the system and method collect, store and display accumulated particle counts from multiple particle measuring instruments. As such, both the process data and the particle measurement data including the accumulated particle counts are provided to a computer network. A converter is therefore provided to convert the particle measurement data including the accumulated particle counts and the other process data to comply with the computer network protocol such that the data is in a readable form. The computer network transmits the particle measurement data including the accumulated particle counts the other process data and stores the data accordingly. The particle measurement data including the accumulated particle counts and the other process data may then be displayed through a graphic user interface.

Additional aspects of the system and method provide for the collecting, storing, and displaying of other particle measurement data. For example, it is advantageous to obtain differential particle counts from the particle measuring instruments. Differential particle counts can be treated in a similar manner as the accumulated particle counts, which include converting the differential particle counts in accordance with a network protocol, transmitting the differential partial counts via the computer network, storing the differential particle counts, and allowing a user to retrieve and display the differential particle counts through the graphic user interface. Other valuable data that is collected, stored and displayed may include instrument data associated with the particle measuring instruments themselves. This data may include a unique device label identifying the respective particle measuring instrument. It may also include date, time, manifold position, and power supply voltage levels associated with each particle measuring instrument and, in turn, with each particle count.

The computer network may include a memory buffer to collect the particle measurement data and the processed data. In this regard, once the data is received via the computer network, a parsing function can parse the data according to its type, such as by separating the different particle counts, instrument data and the process data. The different types of particle counts may then be separately stored in the memory buffer for later retrieval. These instrument data associated with the particle counts may then be used to identify or name the individual particle counts as they are stored.

Another advantageous aspect of the present invention provides for collecting, storing, and displaying accumulated and differential particle counts according to their particle size. In this embodiment, the particle measuring instrument distinguishes the particle measurements according to a predetermined particle size. These particle counts are then collected, stored, and displayed in the same manner as previously discussed. The graphic user interface allows selection of this predetermined particle size, however, such that quality control parameters of the process may be assessed and/or such that the same quality control parameters may be reviewed in a different level of detail.

There are a multitude of possible instruments from which the foregoing system and method may retrieve data. For example, particle measuring instruments that measure particle counts in aerosol mediums, gas mediums, and liquid mediums may be utilized. Additionally, the process data collecting device may collect from devices including a temperature monitoring device, a relative humidity monitoring device, and pressure monitoring device.

The present invention also includes an advantageous method for collecting, storing, and displaying particle measurement data and other process data. With respect to the particle measurement data, accumulated particle counts from particle measuring instruments in remote locations may be collected, stored and displayed. Process data, other than particle counts, is also determined at remote locations by devices that are independent of the particle measuring instruments. The process data may include relative humidity, temperature, and pressure. This process data and particle measurement data including accumulated particle count data may then be transmitted via a computer network for storage and display. In one aspect, the particle measurement data may also include differential particle counts. Both types of particle counts may be discriminated according to particle size.

Therefore, the system and method of the present invention collects a wide variety of data, including both particle measurement data and other process data, in an integrated manner. With respect to the particle measurement data, the system and method collect and analyze accumulated particle counts and, in some embodiments, differential particle counts in order to provide additional information for facility management purposes or the like. As such, the system and method of the present invention provide a tool to enable greater control and more detailed monitoring of a facility, such as a cleanroom.

BRIEF DESCRIPTION OF THE DRAWINGS

Having thus described the invention in general terms, reference will now be made to the accompanying drawings wherein:

DETAILED DESCRIPTION OF PREFERRED EMBODIMENTS

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
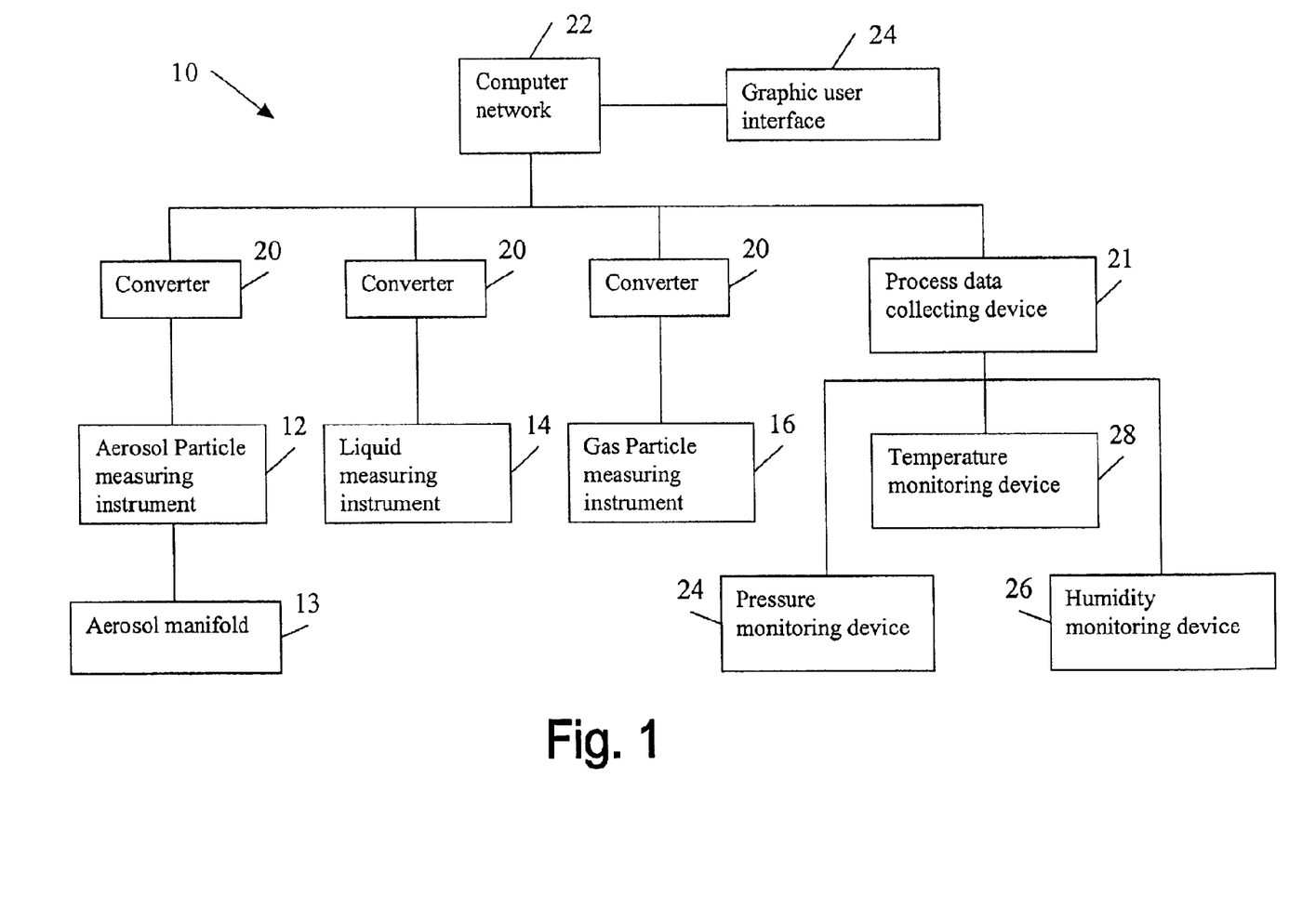
FIG. 1 is a block diagram illustrating a system for collecting, storing, and displaying a plurality of different types of process data, including particle measurement data, according to one embodiment of the present invention.

As depicted in FIG. 1, a system 10 for collecting particle measurement data, from remote locations is provided according to the present invention. While the system, and method of the present invention can collect, display, and store process data for various types of processes, the system and method are particularly well suited for the collection and analysis of a plurality of different types of process data, including particle measurement data, during a wafer fabrication process. For purposes of illustration and not of limitation, the system and method will be subsequently described in conjunction with the collection and analysis of process data, including particle measurement data, during a wafer fabrication process.

The system 10 includes a plurality of particle measurement instruments for collecting particle data. As depicted in FIG. 1, the system can include different types of particle measuring instruments 12, 14, 16, depending upon the environment or the medium in which particles are to be detected. In a wafer fabrication process, for example, it is typically advantageous to detect the particles in several different environments or mediums including the detection of particles in an aerosol such as in a cleanroom, the particles in a liquid, such as ultra-pure water or ultra-pure chemicals, and the particles in a gas, such as hydrogen or nitrogen, that is generally subjected to relatively high pressure.

As such, the illustrated embodiment of the system 10 includes an aerosol particle measuring instrument 12 for monitoring particles and contaminants in an aerosol. One such example is a LASAIR® particle counter produced by Particle Measuring Systems, Inc. LASAIR® particle counters and their equivalents are commonly used to monitor aerosol streams introduced into wafer fabrication cleanrooms. Additionally, an aerosol particle measuring instrument 12 is often used with an aerosol manifold 13 for monitoring a plurality of sampling points throughout a cleanroom. Several such aerosol manifolds 13 are produced by Particle Measuring Systems, Inc., including the Model Nos. AM-12, AM-24, and the AM-30, which sample 12, 24, or 30 locations, respectively. Thus, a single aerosol particle measuring instrument 12 can determine particle counts at a plurality of locations throughout one or more cleanrooms.

Another particle measuring instrument includes a liquid particle measuring instrument 14. These devices measure contaminant particles in liquid streams such as ultra-pure water and various process chemical solutions. Many such liquid particle measuring instruments 14 exist and one such example is the Model HSLIS liquid particle counter produced by Particle Measuring Systems, Inc.

Also included in the particular embodiment is a gas particle measuring instrument 16. These are often used to monitor particle contaminants in high pressure nitrogen and hydrogen environments used in the wafer fabrication process. Many various gas particle measuring instruments 16 may be employed for this purpose. One particular example is the high pressure gas probe provided Particle Measuring Systems, Inc.

Additionally, the system 10 includes monitoring devices for other process data, i.e., process data other than particle counts. Examples include a temperature monitoring device 28 for monitoring the temperatures in relation to various particle sample locations, such as a cleanroom. Pressure monitoring devices 24 may also be employed, for example, in monitoring pressure in high pressure gas environments. A relative humidity monitoring device 26 may also be employed in a similar manner to the other process data devices. All of these and other alternative process data collection devices may be used in the fabrication of wafers and other processes requiring the repeated and precise measurement of different system parameters. The monitoring devices for collecting process data are independent of the particle measuring instruments in that the monitoring devices collect and transmit the other process data without interaction with the particle measuring instruments as in conventional designs. In one embodiment, the process data collected by the various monitoring devices may be collected by a single process data collection device 18, in order to provide a centralized data collection location. Such a process data collection device 18 and a scheme to collect other types of process data are set forth with more detail in U.S. patent application Ser. No. 09/536,506 filed Mar. 27, 2000, the contents of which are expressly incorporated herein in its entirety.

According to the present invention, the system 10 for collecting, storing, and displaying process data includes a computer network 22 for remote access and storage of the particle measurement data and other process data. The computer network 22 provides a connection to the remotely located plurality of particle measuring instruments 12, 14, 16 and the process data collection device 18 or, alternatively, each of the individually monitoring devices for collecting other process data. The computer network 22 may then collect information from each of these devices. After collection of the particle measuring data and the process data, the computer network 22 transmits and stores the data for later access, retrieval, and display.

Preferably, the computer network 22 is a local area network. In one embodiment the network may be an Ethernet network. Many various configurations are available to suit the needs of various industry and commercial network applications. As known to those skilled in the art, most computer networks typically include elements such as a central computer server, other dedicated function and multitask computer servers, various intercommunications devices, switches, routers, electrical cabling, and/or optical cabling.

Display and selection of the particle measuring data and other process data is accomplished through a graphic user interface 24. Many interfaces 24 may be utilized to achieve the functions set forth herein. For example, the interface is typically a display screen and an input device. The display screen can be any monitor, LCD display, LED indicator panel, or any other device that provides visual indication. The input device can be any touch pad, touch screen, push button, keyboard, microphone with voice recognition software, or any other device that can be used to permit a user to supply instructions to the computer network. Oftentimes, as known to those skilled in the art, displays and input devices are unitary devices, such as touch screen displays and push button display panels. In the preferred embodiment, however, the graphic user interface 24 is a computer terminal having network access with a monitor and keyboard, such as a personal computer that is already connected to a multipurpose local area network. Among other things, the graphic user interface permits a user, such as a wafer fabrication quality control supervisor, to provide configuration settings and system operating instructions.

Typically, the computer network 22 operates using a serial data protocol such as TCP/IP. The particle measuring instruments 12, 14, 16, however, do not typically operate using the same network protocol. Therefore, converters 20 are provided which convert particle measuring instrument data from its original protocol to the computer network protocol. In this regard, each converter 20 is associated with a respective particle measuring instrument 12, 14, 16, for converting particle measuring data into the computer network protocol. In one of the various possible embodiments, the converters 20 are servers such as the microserial servers provided by Lantronix, Inc., of Irvine, Calif. Such a serial server converts RS232 compatible serial data streams, such as the above referenced particle counters provided by Particle Measuring Systems, Inc., to TCP/IP. As such, each converter 20 may be given a particular IP address in order for the computer network 22 to specifically identify and query the converter which supplies the particle measuring data.

In operation, the plurality of particle measuring instruments 12, 14, 16, collect particle count samples and provide data for each sample. More specifically, the instruments collect accumulated particle counts, which are the sum of the particle counts measured within a predefined window of time. Additionally, the particle measuring instruments 12, 14, 16, may collect differential particle counts, which are the differential increment or decrement, i.e., the change, in particle count from sample to sample. Accumulated and differential particle counts advantageously aid wafer fabrication quality control supervisors to monitor and analyze quality in the manufacture process. Thus, it is beneficial to collect, store, and display at least the accumulated particle count and, more preferably, both accumulated and differential particle counts, to support and maintain quality control standards in the wafer fabrication process. Since each type of count may be used in different quality control analyses, it also beneficial to provide the quality control supervisor an opportunity to easily configure the system to collect either one or both types of particle counts, i.e., differential or accumulated particle counts. Typically, this selection of the type of particle count(s) to collect, store and display is provided via the graphical user interface 24.

According to one embodiment of the present invention, the preferred particle measuring instruments 12, 14, 16, also count particles according to a predetermined size, i.e., particles larger than a predetermined size. For example, the particle measuring instrument 12, 14, 16, may be set, typically via the graphical user interface 24, with a discrimination setting for particles greater than 0.1 microns. Thus, only particles larger than 0.1 micron are detected by the particle measuring instruments. By permitting a user to select the size of particles to be detected, the system and method permits the process data collection to be tailored pursuant to a particular quality control analysis.

In addition to providing particle measurements, the particle measuring instruments 12, 14, 16, can supply instrument data directly related to the particular operating parameters of the particle measuring instruments 12, 14, 16. Each particle measuring instrument 12, 14, 16 preferably provides a specific identifier, such as a label, to distinguish its samples from samples collected by other particle measuring instruments. Ultimately, the computer network 22 can associate each particle measurement with the device location and type based upon the label. For example, a wafer fabricator may designate a particle measuring instrument 12, 14, 16, with shorthand abbreviations according to the sample type, the room, and the building where the device is located.

As described above, many of the commercially available particle measuring instruments 12 may sample from a plurality of locations via a manifold 13. In this regard, these particle measuring instruments 12 also provide manifold position data in order to determine the specific sample location. Additionally, the particle measuring instruments 12, 14, 16, can provide a date and time coincident to each measured particle sample. Furthermore, the particle measuring instruments 12, 14, 16, operate from narrowly regulated voltage supplies. The quality of their operation and the quality of their sample determination is dependent upon power supply voltage. Thus, it is advantageous for each particle measuring instrument 12, 14, 16, to provide its particular power supply voltage. As will be evident, it is beneficial to collect and store the foregoing instrument data in order to identify each sample.

Thus, the present invention provides a system and method of collecting, storing, and displaying particle measurement data including accumulated particle counts and, in some embodiments, differential particle counts, process data other than particle measurement data, and, at least in some embodiments, particle measuring instrument data. Additionally, the system and method permit a quality control supervisor to select from among the foregoing data for display and storage purposes, typically via a graphical user interface 24. As known to those skilled in the art, quality control measures and analyses continually change according to a multitude of production and process parameters. Thus, what is desired and optimum quality control data one day may not be desired and optimum the next day. Therefore, providing quality control supervisors the opportunity to select analysis data from among a plurality of particle measuring instruments and other process data collection devices through a remote graphic interface is beneficial.

Figure 2:
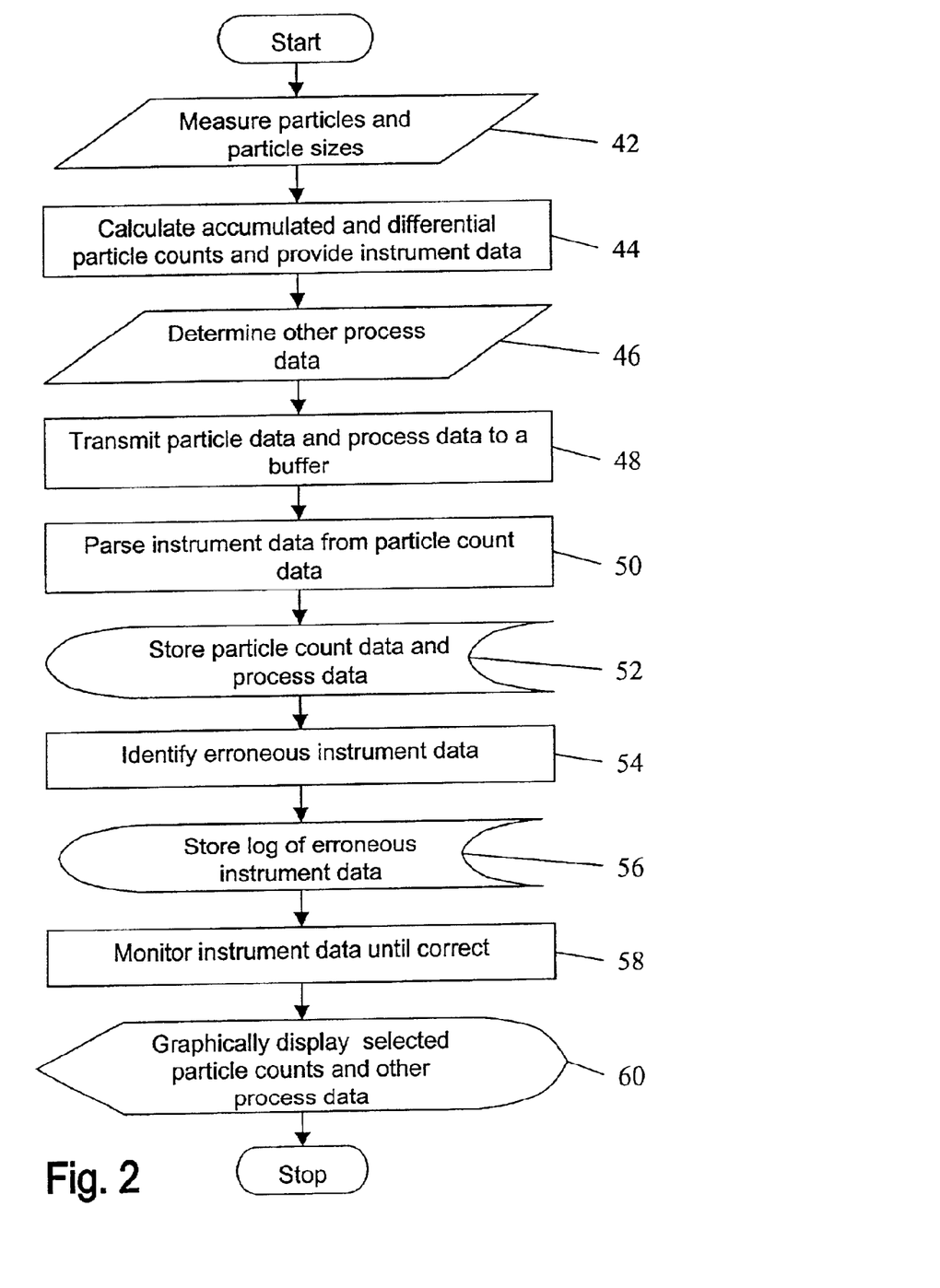
FIG. 2 is a flow chart illustrating operations performed by the system and method of one embodiment of the present invention.

In this regard, FIGS. 1 and 2 are block diagram and control flow illustrations of methods and systems according to the invention. It will be understood that each block or step of the block diagram and control flow illustrations, and combinations of blocks in the block diagram and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram or control flow blocks or steps. These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram or control flow blocks or steps. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram or control flow blocks or steps.

Accordingly, blocks or steps of the block diagram or control flow illustrations support combinations of means for performing the specified functions, combinations of steps for performing the specified functions and program instruction means for performing the specified functions. It will also be understood that each block or step of the block diagram or control flow illustrations, and combinations of blocks or steps in the block diagram or control flow illustrations, can be implemented by special purpose hardware-based computer systems which perform the specified functions or steps, or combinations of special purpose hardware and computer instructions.

To this end, FIG. 2 illustrates the control flow application of the present invention according to one particular embodiment. As shown, particle counts are measured by particle measuring instruments 12, 14, 16. See block 42. Typically, the particle counts are determined according to particle size. In order to determine the accumulated particle counts, the sum of the particle counts collected during a predefined window of time, conversely, each sample may also be compared sample to sample to determine differential particle counts. See block 44. Additionally, for each sample, the particle measuring instrument 12, 14, 16, preferably provides instrument data defining the instrument which collected the respective sample. The particle measuring instrument 12, 14, 16, then provides the particle measurement data including the accumulated particle counts and coincident instrument data to the computer network 22. Concurrently, other process data, independent of the particle measurement data, is determined by the process data collection device 18, which is also provided to the computer network 22. See block 46. As previously discussed, the process data collection device 18 and each converter 20 associated with a respective particle measuring instrument 12, 14, 16, may be given a particular TCP/IP address. As such, the computer network 22 may serially examine each address and retrieve particle measurement data, instrument data, and other process data. See block 48. This data may be transmitted via the computer network to a memory buffer wherein the data is at least temporarily stored while awaiting further processing by the computer network 22. See block 52.

The computer network 22 provides a means for parsing the instrument data from the particle measurement data prior to storage in a database. See blocks 50 and 52. In this regard, each particle sample is preferably associated with the instrument data defining the instrument which collected the particle sample. Thus, the particle measurement data can be stored in a database in association with the corresponding instrument data. For example, the particle measurement data may be stored in association with a name defining the instrument which collected the particle sample.

Additionally, the instrument data may be used by the computer network 22 to determine whether the particle measuring instrument 12, 14, 16, has provided an erroneous reading. See block 54. In this regard, instrument data can be expected to provide relatively consistent and predictable data, including date, time, voltage, and manifold position. Establishing expected data parameters to be recognized by the computer network 22 then provides a reliable indicator of proper operation of the particle measuring instruments 12, 14, 16. When the instrument data is outside any of the established parameters, the computer network 22 can then flag the instrument data and particle measurement data as erroneous. See block 54. Upon recognizing erroneous instrument data, the computer network 22 may be instructed to disregard readings from that particular particle measuring instrument while continuing to collect, store, and display other particle measurement data. More specifically, the computer network 22 may be instructed to log and store the erroneous reading in a database for later access and review of the faults. See block 56. This error log may be stored in the same database as the aforementioned particle measurement data and instrument data, or a separate and independent database.

Figure 3:
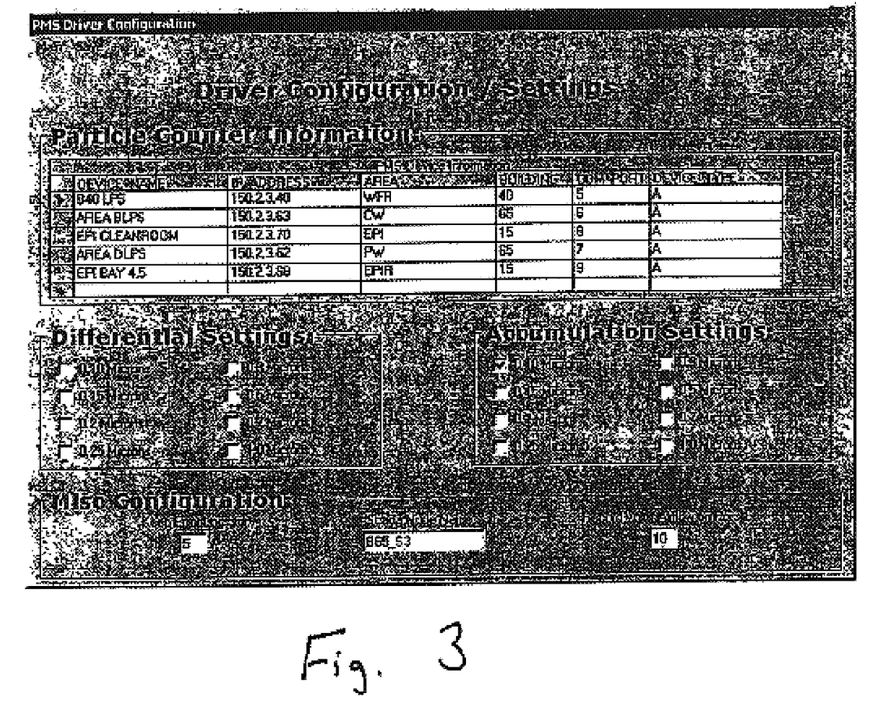
FIG. 3 is a screen display generated by the system and method of one embodiment of the present invention illustrating the selection of accumulated counts, differential counts, and particle size provided by the graphic user interface.

FIG. 3 represents one example of a graphic user interface 24 that permits the configuration of each particle measuring instrument 12, 14, 16, according to one embodiment of the invention. The heading "Particle Counter Information" provides the device label of each particular particle measuring instrument 12, 14, 16, in tabular form. Although the particle measurement instruments 12, 14, 16, can be labeled in various fashions, the particle measuring instruments 12, 14, 16, are normally labeled based upon the room or zone of a room in which the particle measuring instrument is located and/or the stage of the process that is being monitored by the particle measuring instrument. For example, the device label B40 LPS represents a liquid particle measuring instrument 14 in building number 40.

In one embodiment, the graphic user interface 24 may be a monitor, keyboard, and/or a computer terminal to allow the user to graphically select a particular device from the tabular listing via the interface. Upon selection of a particular device to configure, the user may then select the size of the particles to count under either "differential settings" or "accumulation settings", which instructs the system to collect, store and display particle counts according to differential counts or accumulated counts, respectively. Each type of particle count provides a variety of particle sizes from which to discriminate among accumulated particle and differential particle counts. FIG. 3 is an example of eight different particle size settings, from 0.10 microns up to 1.0 microns. Additionally, the particle measuring system and method need not be limited to just one selection of particle size for each different type of particle count, but may provide for the selection of a plurality of particle size settings, both for differential and accumulated particle counts. For example, a differential setting of 0.25 microns and an accumulation setting of 0.10 and 0.3 microns may be selected for the particular particle measuring instrument. Consequently, differential particle counts of all particles larger than 0.25 microns, accumulated particle counts of all particles larger than 0.10 microns, and accumulated particle counts of larger than 0.3 microns will all be collected for subsequent storage and display.

Typically, the blocks of the database are reserved based upon the individual particle measuring instrument providing the data. For example, the storage of a particular type of data may be in a predefined area of memory based upon the particular instrument that collects the particle measurement data as defined above. Additionally, instrument data may also be stored in the defined block in association with the particle measurement data. The process data provided by the process data collection devices is typically identified based upon the monitoring device that obtained the process data and may be stored in the same fashion as described above in conjunction with the particle measurement data.

The example of the configuration display in FIG. 3 provided by the graphical user display 24 may also permit the configuration of various miscellaneous parameters. As shown, the period of time for which the error log is maintained may be defined. In addition, a network incorporating a Supervisory Control and Data Acquisition (SCADA) system will generally provide multiple computers in the network that may be selected to process the particle data. The heading "SCADA Node Name" provides configuration of the computer network for selecting the particular computer that will receive and process the particle data. Another configurable parameter includes the recording of the particle measuring instrument voltage and, for aerosol particle measuring instruments, the airflow. In this particular embodiment, these parameters are required to be recorded to the database only once for a cycle of aerosol manifold readings. Therefore, as shown in FIG. 3, voltage and airflow readings will only be recorded concurrently with the manifold port number reading at port number 10.

Figure 4:
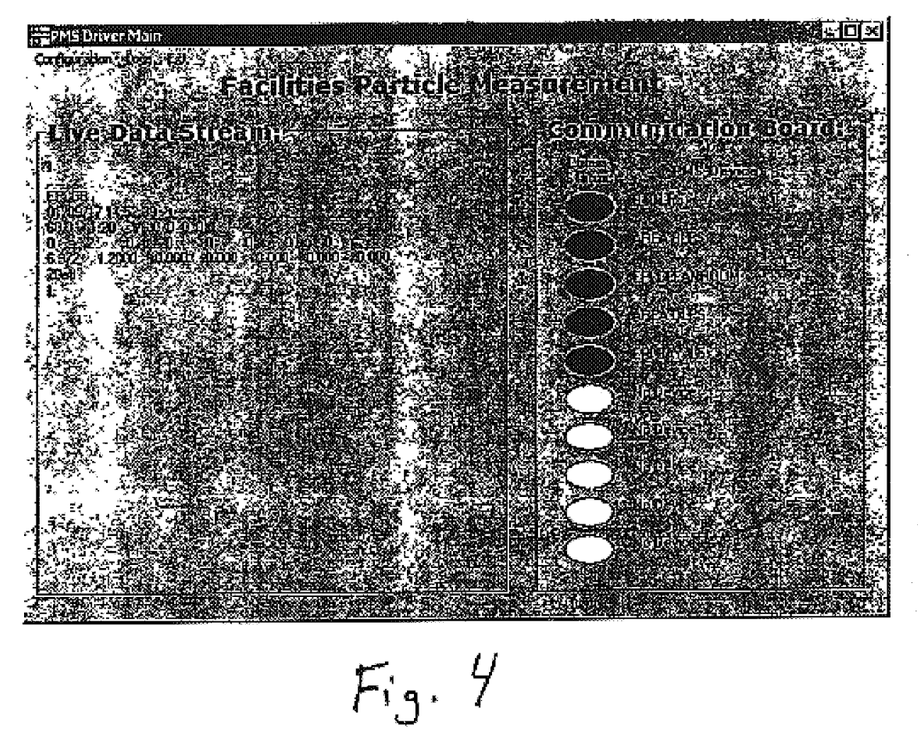
FIG. 4 is a screen display generated by the system and method of one embodiment of the present invention illustrating the communication status of each particle measuring instrument.

The graphic user interface 24 may also display the data collected by one or more of the particle measurement devices and/or the process data collection devices, one example of which is depicted in FIG. 4. This particular embodiment provides a display for viewing both the particle count and instrument data, and the communications status of each particle measuring instrument. For example, "Live Data Stream" represents a real time display of unprocessed data currently being read from a particle measuring instrument. As such, "AREA BLPS" in the first line represents the particle measuring instrument device name. The second line represents the date and time of the current reading. The third line represents miscellaneous firmware parameters of the particle measuring instrument and the manifold port number being read. The fourth line represents the number of particle counts corresponding to particle size, each column corresponding to one of the eight possible particle sizes previously discussed. For purposes of illustration, each number is set to zero but will display an actual particle count during operation. The fifth line represents instrument airflow and instrument voltage readings in the first and second column, respectively. The final line represents an assigned identification number for the transmission associated therewith.

The heading "Communication Board" in the exemplary display of FIG. 4, illustrates the communication status of each particle measuring instrument 12, 14, 16, according to the aforementioned instrument data operating parameters. The "PMS Device" column lists the designated names for each particle measuring instrument 12, 14, 16. The "Comm Status" column provides a graphic representation of whether the instrument data associated with the respective particle measuring instrument is within the operating parameters. As such, when the instrument data is erroneous, the ellipse next to the instrument name would be filled with a first color, such as red which creates a darker black color in FIG. 4. On the other hand, the ellipse next to the instrument name would be filled with a second color, such as green which creates a lighter gray color in FIG. 4 if the instrument data is within the operating parameters. Obviously, other techniques for depicting the validity of the data collected by a respective particle measurement device may be employed, if so desired.

Therefore, a system and method for collecting, storing, and displaying process data, including particle measurement data, and, in particular, accumulated particle counts, is provided. The system and method permit the collection of process data from various remote locations and the transmission of the process data via a computer network 22. The system and method also permit the particle measuring instruments 12, 14, 16, to be configured and the process data to be reviewed, typically via a graphical user interface 24. Accordingly, the system and method of the present invention are well suited for the collection of particle measurement data and other process data unrelated to particle measurement data during wafer fabrication in order to permit a technician to perform quality control analyses in a central location.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for collecting, storing, and displaying particle measurement data comprising:

a plurality of particle measuring instruments for repeatedly measuring the number of particles and for determining an accumulated particle count and a differential particle count based upon a plurality of measurements;

a plurality of converters for converting the accumulated particle counts and differential particle counts provided by the plurality of particle measuring instruments in accordance with a computer network protocol and providing the accumulated particle counts following conversion in accordance with the computer network protocol;

a process data collection device for providing process data from other than particle measuring instruments;

a computer network for receiving and storing the accumulated particle counts and differential particle counts and the process data, said computer network receiving the process data from said process data collection device in a manner independent of said particle measuring instruments; and a graphic user interface for displaying and retrieving at least some of the accumulated particle counts, differential particle counts, or process data.

2. A system according to claim 1 wherein said plurality of particle measuring instruments also determine instrument data based on particle measuring instrument operating parameters and said converter converts said instrument data in accordance with the computer network protocol and provides the instrument data following conversion to the computer network.

3. A system according to claim 2 wherein said instrument data is based on operating parameters selected from the group consisting of a device label, a date, a time, a manifold position, and a power supply voltage.

4. A system according to claim 3 wherein said computer network includes a memory buffer for collecting accumulated particle count and instrument data, a parser for distinguishing the instrument data and accumulated particle counting data, and a database for individually storing said particle count and instrument data following parsing.

5. A system according to claim 4 wherein said computer network stores said particle count data in the database and associates a respective name with the particle count data according to said instrument data relating thereto.

6. A system according to claim 3 wherein said computer network includes a fault identifier which detects and monitors erroneous instrument data.

7. A system according to claim 6 wherein said graphic user interface provides a graphic representation of the erroneous instrument data.

8. A system according to claim 1 wherein said plurality of particle measuring instruments determine accumulated particle counts in accordance with a predetermined particle size.

9. A system according to claim 8 wherein said plurality of particle measuring instruments determine differential particle counts in accordance with the predetermined particle size.

10. A system according to claim 8 wherein said graphic user interface permits definition of the predetermined particle size and subsequently displays the accumulated particle count in accordance with the predetermined particle size.

11. A system according to claim 1 wherein the process data collection device collects data from at least one of a relative humidity monitoring device, a temperature monitoring device, and a pressure monitoring device.

12. A system according to claim 1 wherein said plurality of particle measuring instruments are selected from the group consisting of an aerosol particle measuring instrument, a gas measuring device, and a liquid particle measuring instrument.

* * * * *

UNITED STATES PATENT AND TRADEMARK OFFICE
CERTIFICATE OF CORRECTION

PATENT NO. : 6,773,932 B2
DATED : August 10, 2004
INVENTOR(S) : Robinson et al.

It is certified that error appears in the above-identified patent and that said Letters Patent is hereby corrected as shown below:

Title page,
Item [73], Assignee, "Seh America, Inc." should read -- SEH America, Inc. --.

Drawings,
Sheets 3 and 4 should be deleted to be substituted with the attached sheets 3 and 4.

Signed and Sealed this

Thirtieth Day of November, 2004

JON W. DUDAS
*Director of the United States Patent and Trademark Office*

PMS Driver Configuration

Main  Save

Driver Configuration / Settings

Particle Counter Information:

| PMS Device Information | | | | | |
|---|---|---|---|---|---|
| DEVICE NAME | IP ADDRESS | AREA | BUILDING | COM PORT | DEVICE TYPE |
| ▶ B40 LPS | 150.2.3.40 | WFR | 40 | 5 | A |
| AREA BLPS | 150.2.3.63 | CW | 65 | 6 | A |
| EPI CLEANROOM | 150.2.3.70 | EPI | 15 | 8 | A |
| AREA DLPS | 150.2.3.62 | PW | 65 | 7 | A |
| EPI BAY 4.5 | 150.2.3.68 | EPIR | 15 | 9 | A |
| * | | | | | |

Differential Settings:
- ☐ 0.10 Microns     ☐ 0.3 Microns
- ☐ 0.15 Microns     ☐ 0.5 Microns
- ☐ 0.2 Microns       ☐ 0.7 Microns
- ☐ 0.25 Microns     ☐ 1.0 Microns

Accumulation Settings:
- ☑ 0.10 Microns     ☐ 0.3 Microns
- ☐ 0.15 Microns     ☐ 0.5 Microns
- ☐ 0.2 Microns       ☐ 0.7 Microns
- ☐ 0.25 Microns     ☐ 1.0 Microns

Misc Configuration:

| Keep Error Logs for | Scada Node Name: | Record Volt / Airflow on Port #: |
|---|---|---|
| [5] days | [865_S3] | [10] |

FIG. 3

FIG. 4